United States Patent [19]

Suzuki

[11] Patent Number: 4,957,662

[45] Date of Patent: Sep. 18, 1990

[54] METHOD FOR PURIFYING FATTY ACIDS

[76] Inventor: Masao Suzuki, 2-25-B2-406 Kasaya-Cho, Nishinomiya City, Hyogo Pref., Japan

[21] Appl. No.: 76,829

[22] Filed: Sep. 19, 1979

[30] Foreign Application Priority Data

Sep. 27, 1978 [JP] Japan ................................ 53-118024

[51] Int. Cl.[5] ................................................ C11C 1/08

[52] U.S. Cl. .................................................... 260/419

[58] Field of Search ................................ 260/409, 419

[56] References Cited

U.S. PATENT DOCUMENTS

| | | | |
|---|---|---|---|
| 2,056,984 | 10/1936 | Schellmann | 260/419 |
| 2,216,238 | 10/1940 | Harder | 260/419 |
| 2,727,916 | 12/1955 | Logan | 260/419 |
| 2,763,638 | 9/1956 | Nevin | 260/419 |
| 2,872,464 | 2/1959 | Brown | 260/419 |
| 3,833,629 | 9/1974 | Naskar | 260/419 |

*Primary Examiner*—John F. Niebling

[57] ABSTRACT

Fatty acids having excellent color and color stability can be obtained by a combination procedure of a contacting step of a crude fatty acid with a reducing metal, and a distillation step.

4 Claims, No Drawings

METHOD FOR PURIFYING FATTY ACIDS

BACKGROUND OF THE INVENTION (1) Field of the Invention:

The present invention relates to a method of purifying fatty acids in order to obtain fatty acids having excellent color and color stability.

(2) Description of the Prior Art:

There are generally known, as a method of purifying fatty acids, adsorption method using activated clay or active carbon, and further methods using polycarboxylic acid (Japanese Patent Laid Open Application No. 4,277/72), boric acid (U.S. Pat. No. 2,862,943), sulfuric acid (U.S. Pat. No. 3,489,779), boron trifluoride (U.S. Pat. No. 2,583,028), amino compound (U.S. Pat. No. 3,471,536), formaldehyde (U.S. Pat. No. 3,066,160), a combination system of an alkaline substance, hypophosphorous acid and boric acid (Japanese Patent Application Publication No. 16,506/71) and a combination system of organic amine and phenolic compound (Japanese Patent Application Publication No. 46,205/77 and No. 7,408/78). In these methods, a part of the coloring substances contained in fatty acid can be removed, but sufficiently light-colored fatty acid can not be obtained, and further impurities, which color due to heat, oxidation or acidic or basic reagent, can not be completely removed. Therefore, the fatty acids purified by the above described methods often color during storage and further the derivatives of the fatty acid often color. Moreover, some of the above described reagents are dangerous or poisonous.

The inventor has made various investigations for developing a method of purifying fatty acids, which is free from the drawbacks of the above described conventional methods, and found out a purification method having a high purification efficiency which can be carried out by the use of a safe and substantially non-toxic reagent.

SUMMARY OF THE INVENTION

The aspect of the method for purifying fatty acids according to the present invention lies in the combination procedure of a contacting step of a fatty acid with a reducing metal, and a distillation step.

That is, the feature of the present invention lies in a method of purifying fatty acids, comprising contacting a fatty acid with a reducing metal, and distilling the treated fatty acid.

DESCRIPTION OF THE PREFERRED EMBODIMENTS

The fatty acid to be applied to the present invention includes fatty acids having about 6–24 carbon atoms, which are obtained by the hydrolysis of natural fats and oils, such as animal fats and oils, vegetable fats and oils, and fish oil, or otained by synthetic methods, such as paraffin oxidation process, oxo process, oxidation cleavage process, skeletal isomerization process and the like. These fatty acids are, for example, coconut oil fatty acid, palm oil fatty acid, soybean oil fatty acid, tall oil fatty acid, tallow fatty acid, sardine oil fatty acid, valeric acid, caproic acid, caprylic acid, pelargonic acid, capric acid, lauric acid, myristic acid, palmitic acid, stearic acid, oleic acid, linoleic acid, linolenic acid, arachidic acid, behenic acid, erucic acid, lignoceric acid, 2-ethylhexanoic acid, isostearic acid and the like.

According to the present invention, when a mixture of a reducing metal and a hydroxide of reducing metal is used in place of a reducing metal alone the purification effect improves.

Further, when a mixture of a reducing metal and a hydrogenation catalyst is used, the purification effect more improves.

When a mixture of a reducing metal, a hydroxide of reducing metal and a hydrogenation catalyst is used, the purification effect is remarkably high.

In the present invention, the fatty acid to be purified must be contacted with the above described reagent for purifying fatty acid, at a temperature of from room temperature to 300° C., preferably at a temperature of 80°–250° C.

The contacting time is not particularly limited, but is generally 0.5–10 hours.

According to the present invention, the object for purifying fatty acid can be easily attained by adding the reagent to a fatty acid and distilling directly the resulting mixture. In this case, when the mixture of a fatty acid and the reagent is heated under the above described condition, a more preferable result can be obtained.

When it is intended to avoid the formation of a large amount of distillation residue in the distillation vessel, the above described reagent is added to a fatty acid, the resulting mixture is fully mixed within the above described temperature range under stirring and then filtered to remove insoluble reaction product and unreacted reagent, and the filtrate is distilled.

As the reducing metal, there are used tin, iron, zinc, aluminum, magnesium, copper, calcium, nickel, cobalt and the like, and mixtures and alloys thereof. The reducing metal is preferably used in the form of powder.

As the hydroxide of reducing metal, there are used tin hydroxide, iron hydroxide, zinc hydroxide, aliminum hydroxide, magnesium hydroxide, copper hydroxide, calcium hydroxide, nickel hydroxide, cobalt hydroxide and the like, and mixtures thereof.

The hydrogenation catalyst is a catalyst used in the hydrogenation of organic compound, and includes iron, cobalt, nickel, ruthenium, rhodium, palladium, osmium, iridium, platinum, chromium, molybdenum, tungsten, copper, rhenium, vanadium and the like, and their alloys, and their compounds, such as oxide, hydroxide, sulfide and the like. The alloys and compounds are palladium black, palladium on carbon, platinum oxide, nickel on kieselguhr, Raney nickel, Raney iron, Raney copper, copper-chromite, molybdenum sulfide and the like.

Each of the above described reducing metal, the hydroxide of reducing metal and the hydrogenation catalyst can be used in the form of a mixture.

The use amount of the reducing metal, the hydroxide of reducing metal and the hydrogenation catalyst can be varied over a wide range and is not particularly limited. However, each of the reducing metal, the hydroxide of reducing metal and the hydrogenation catalyst is preferably used in an amount of 0.01–5% by weight based on the amount of a fatty acid to be purified. When the amount is less than 0.01% by weight, the purification effect is poor, while even when the amount exceeds 5% by weight, the purification effect is not so improved, and when such large amount is used, the distillation residue rather increases.

The reducing metal to be used in the present invention probably reduces colored, ill-ordered or coloring oxygen-containing impurities, such as carbonyl compound, hydroxyl compound, epoxy compound, phenolic compound and the like, contained in fatty acid.

The hydroxide of reducing metal probably enhances mainly the reducing ability of the reducing metal.

Further, the hydrogenation catalyst probably promotes the reduction reaction by the reducing metal and further acts as a catalyst for the reduction reaction by the hydrogen generated in the reaction of the fatty acid with the reducing metal. Accordingly, when a reducing metal is used in combination with a hydroxide of reducing metal and a hydrogenation catalyst, the reducing metal acts remarkably effectively.

Substantially all the reducing metal and the hydroxide of reducing metal used in the purification of fatty acid are finally converted into fatty acid salt, and the fatty acid salt is removed by filtration or in the form of a distillation residue. The hydrogenation catalyst also is removed by filtration or in the form of distillation residue.

The purified fatty acid obtained in the present invention does not substantially contain oxygen-containing impurities, and therefore the fatty acid is light in the color and has not unpleasant odor, and further has an excellent color stability against heat, oxidation and acidic and basic reagents.

The following examples are given for the purpose of illustration of this invention and are not intended as limitations thereof.

In the examples, a method, wherein a reducing metal alone is used as a reagent for purifying fatty acid, is referred to as "Method A"; a method, wherein a mixture of a reducing metal and a hydroxide of reducing metal is used as the reagent, is referred to as "Method B"; a method, wherein a mixture of a reducing metal and a hydrogenation catalyst is used as the reagent, is referred to as "Method C"; and a method, wherein a mixture of a reducing metal, a hydroxide of reducing metal and a hydrogenation catalyst is used as the reagent, is referred to as "Method D".

Further, in the following examples, a fraction up to a bottom temperature of 230° C. under 1 mm Hg was gathered. However, in Example 9, a fraction up to a bottom temperature of 150° C. under 1 mm Hg was gathered.

EXAMPLE 1

(Method A) To 300 g of a crude coconut oil fatty acid was added 2.0 g of tin powder, and the resulting mixture was directly distilled to obtain a purified coconut oil fatty acid.

(Method B) To 300 g of the same crude coconut oil fatty acid as used in Method A were added 2.0 g of tin powder and 1.0 g of zinc hydroxide, and the resulting mixture was directly distilled to obtain a purified coconut oil fatty acid.

(Method C) To 300 g of the same crude coconut oil fatty acid as used in Method A were added 2.0 g of tin powder and 0.3 g of a platinum-on-carbon catalyst, and the resulting mixture was stirred at 120° C. for 4 hours. Then, the mixture was filtered, and the filtrate was distilled to obtain a purified coconut oil fatty acid.

(Method D) To 300 g of the same crude coconut oil fatty acid as used in Method A were added 2.0 g of tin powder, 1.0 g of zinc hydroxide and 0.3 g of a platinum-on-carbon catalyst, and the resulting mixture was stirred at 120° C. for 4 hours. Then, the mixture was filtered, and the filtrate was distilled to obtain a purifieid coconut oil fatty acid.

(Comparative method) 300 g of the same crude coconut oil fatty acid as used in method A was distilled without the addition of the reagent to obtain a distilled coconut oil fatty acid.

The above purified coconut oil fatty acids were tested with respect to the yield, color, color stabilities against heat and oxidation and color stabilities against acidic and basic reagents. The obtained result is shown in the following Table 1.

TABLE 1

| Item | Comparative method | Method A | Method B | Method C | Method D |
|---|---|---|---|---|---|
| (1) Distillation yield (wt. %) | 95.3 | 93.8 | 93.4 | 93.7 | 93.2 |
| (2) Color (APHA) | 200 | 60 | 40 | 30 | 20 |
| (3) Heat color stability (APHA) | 400 | 150 | 100 | 70 | 50 |
| (4) Thermal oxidation color stability (APHA) | >500 (Gardner: 4) | 200 | 160 | 130 | 110 |
| (5) Base color stability (APHA) | >500 (Gardner: 4) | 200 | 150 | 110 | 90 |
| (6) Acid color stability (Gardner) | 4 | 3 | 2–3 | 2 | 1–2 |

Note:
A sample having a larger color value colors more noticeably and is poorer in the quality.

The test items (3)–(6) in above Table 1 and the following tables are as follows.

Item (3) shows the color stability of fatty acid against heat. A color value of a fatty acid is measured after the fatty acid is heated at 205° C. for 1 hour under nitrogen atmosphere.

Item (4) shows the color stability of fatty acid against thermal oxidation. A color value of a fatty acid is measured after the fatty acid is heated at 150° C. for 3 hours under the air.

Item (5) shows the color stability of fatty acid against alkaline reagent. A color value of a fatty acid is measured after the fatty acid is heated at 150° C. for 2 hours together with equimolar amount of diethanolamine under stirring by gaseous nitrogen.

Item (6) shows the color stability of fatty acid against acidic reagent. A color value of a fatty acid is measured after the fatty acid is heated at 205° C. for 1 hour together with 0.1% of paratoluenesulfonic acid while stirring by gaseous nitrogen, and then left to stand to be cooled for 1 hour at room temperature.

EXAMPLE 2

(Method A) To 300 g of a crude tallow fatty acid was added 2.0 g of iron powder, and the resulting mixture was directly distilled to obtain a purified tallow fatty acid.

(Method B) To 300 g of the same crude tallow fatty acid as used in Method A were added 2.0 g of iron powder and 0.6 g of iron (III) hydroxide, and the resulting mixture was directly distilled to obtain a purified tallow fatty acid.

(Method C) To 300 g of the same crude tallow fatty acid as used in Method A were added 2.0 g of iron powder and 0.6 g of a nickel-on-kieselguhr catalyst, and the resulting mixture was directly distilled to obtain a purified tallow fatty acid.

(Method D) To 300 g of the same crude tallow fatty acid as used in Method A were added 2.0 g of iron powder, 0.6 g of iron (III) hydroxide and 0.6 g of a nickel-on-kieselguhr catalyst, and the resulting mixture was directly distilled to obtain a purified tallow fatty acid.

(Comparative method) 300 g of the same crude tallow fatty acid as used in Method A was distilled without the addition of the reagent to obtain a distilled tallow fatty acid.

The result of the test of the above purified tallow fatty acids is shown in the following Table 2.

TABLE 2

| Item | Comparative method | Method A | Method B | Method C | Method D |
|---|---|---|---|---|---|
| (1) Distillation yield (wt. %) | 94.5 | 93.2 | 92.1 | 92.9 | 91.8 |
| (2) Color (APHA) | 200 | 60 | 40 | 40 | 30 |
| (3) Heat color stability (APHA) | 400 | 130 | 90 | 80 | 60 |
| (4) Thermal oxidation color stability (APHA) | >500 (Gardner: 5) | 250 | 190 | 160 | 140 |
| (5) Base color stability (APHA) | >500 (Gardner: 5) | 200 | 160 | 140 | 120 |
| (6) Acid color stability (Gardner) | 5 | 3 | 2 | 2 | 1–2 |

EXAMPLE 3

(Method A) To 300 g of a crude oleic acid was added 1.5 g of zinc powder, and the resulting mixture was directly distilled to obtain a purified oleic acid.

(Method B) To 300 g of the same crude oleic acid as used in Method A were added 1.5 g zinc powder and 0.5 g of magnesium hydroxide, and the resulting mixture was directly distilled to obtain a purified oleic acid.

(Method C) To 300 g of the same crude oleic acid as used in Method A were added 1.5 g of zinc powder and 0.6 g of a nickel-hardened fat catalyst (nickel catalyst dispersed in hardened fat), and the resulting mixture was stirred at 150° C. for 4 hours. Then, the mixture was filtered, and the filtrate was distilled to obtain a purified oleic acid.

(Method D) To 300 g of the same crude oleic acid as used in Method A were added 1.5 g of zinc powder, 0.5 g of magnesium hydroxide and 0.6 g of a nickel-hardened fat catalyst, and the resulting mixture was stirred at 150° C. for 4 hours. Then, the mixture was filtered, and the filtrate was distilled to obtain a purified oleic acid.

(Comparative method) 300 g of the same crude oleic acid as used in Method A was distilled without the addition of the reagent to obtain a distilled oleic acid.

The result of the test of the above purified oleic acids is shown in the following Table 3.

TABLE 3

| Item | Comparative method | Method A | Method B | Method C | Method D |
|---|---|---|---|---|---|
| (1) Distillation yield (wt. %) | 92.3 | 90.1 | 89.0 | 90.0 | 88.7 |
| (2) Color (APHA) | 250 | 60 | 40 | 30 | 20 |
| (3) Heat color stability (APHA) | 400 | 110 | 80 | 70 | 60 |
| (4) Thermal oxidation color stability (APHA) | >500 (Gardner: 6) | 250 | 200 | 170 | 150 |
| (5) Base color stability (APHA) | >500 (Gardner: 5) | 350 | 250 | 180 | 160 |
| (6) Acid color stability (Gardner) | 9 | 5 | 4 | 3–4 | 3 |

EXAMPLE 4

(Method A) To 300 g of a crude stearic acid was added 1.2 g of magnesium powder, and the resulting mixture was stirred at 160° C. for 4 hours. Then, the mixture was directly distilled to obtain a purified stearic acid.

(Method B) To 300 g of the same crude stearic acid as used in Method A were added 1.2 g of magnesium powder and 0.5 g of tin (II) hydroxide, and the resulting mixture was stirred at 160° C. for 4 hours. Then, the mixture was directly distilled to obtain a purified stearic acid.

(Method C) To 300 g of the same crude stearic acid as used in Method A were added 1.2 g of magnesium powder, 0.6 g of a Raney copper catalyst, and the resulting mixture was stirred at 160° C. for 4 hours. Then, the mixture was directly distilled to obtain a purified stearic acid.

(Method D) To 300 g of the same crude stearic acid as used in Method A were added 1.2 g of magnesium powder, 0.5 g of tin (II) hydroxide and 0.6 g of a Raney copper catalyst, and the resulting mixture was stirred at 160° C. for 4 hours. Then, the mixture was directly distilled to obtain a purified stearic acid.

(Comparative method) 300 g of the same crude stearic acid as used in Method A was distilled without the addition of the reagent to obtain a distilled stearic acid.

The result of the test of the above purified stearic acids is shown in the following Table 4.

TABLE 4

| Item | Comparative method | Method A | Method B | Method C | Method D |
|---|---|---|---|---|---|
| (1) Distillation yield (wt. %) | 94.2 | 93.0 | 92.3 | 92.8 | 92.1 |

TABLE 4-continued

| Item | Comparative method | Method A | Method B | Method C | Method D |
|---|---|---|---|---|---|
| (2) Color (APHA) | 150 | 40 | 30 | 30 | 20 |
| (3) Heat color stability (APHA) | 300 | 90 | 70 | 60 | 50 |
| (4) Thermal oxidation color stability (APHA) | >500 (Gardner: 5) | 190 | 130 | 100 | 80 |
| (5) Base color stability (APHA) | >500 (Gardner: 3–4) | 190 | 140 | 100 | 80 |
| (6) Acid color stability (Gardner) | 5 | 3 | 2 | 1–2 | 1 |

EXAMPLE 5

(Method A) To 300 g of a commercial tall oil fatty acid was added 3.0 g of calcium, and the resulting mixture was directly distilled to obtain a purified tall oil fatty acid.

(Method B) To 300 g of the same commercial tall oil fatty acid as used in Method A were added 3.0 g of calcium and 1.0 g of calcium hydroxide, and the resulting mixture was directly distilled to obtain a purified tall oil fatty acid.

(Method C) To 300 g of the same commercial tall oil fatty acid as used in Method A were added 3.0 g of calcium and 0.6 g of a copper-chromite catalyst, and the resulting mixture was stirred at 150° C. for 4 hours. Then, the mixture was directly distilled to obtain a purified tall oil fatty acid.

(Method D) To 300 g of the same commercial tall oil fatty acid as used in Method A were added 3.0 g of calcium, 1.0 g of calcium hydroxide and 0.6 g of a copper-chromite catalyst, and the resulting mixture was stirred at 150° C. for 4 hours. Then, the mixture was directly distilled to obtain a purified tall oil fatty acid.

(Comparative method) 300 g of the same commercial tall oil fatty acid as used in Method A was distilled without the addition of the reagent to obtain a distilled tall oil fatty acid.

The result of the test of the above purified tall oil fatty acids is shown in the following Table 5.

TABLE 5

| Item | Comparative method | Method A | Method B | Method C | Method D |
|---|---|---|---|---|---|
| (1) Distillation yield (wt. %) | 98.8 | 97.1 | 95.3 | 95.5 | 93.4 |
| (2) Color (APHA) | 400 | 140 | 110 | 90 | 70 |
| (3) Heat color stability (APHA) | >500 (Gardner: 5) | 180 | 150 | 130 | 110 |
| (4) Thermal oxidation color stability (Gardner) | 6 | 2–3 | 2 | 1–2 | 1–2 |
| (5) Base color stability (Gardner) | 8 | 2–3 | 1–2 | 1–2 | 1 |
| (6) Acid color stability (Gardner) | 10 | 8 | 6–7 | 6 | 5 |

EXAMPLE 6

(Method A) To 300 g of a commercial soybean oil fatty acid was added 1.5 g of aluminum powder, and the resulting mixture was directly distilled to obtain a purified soybean oil fatty acid.

(Method B) To 300 g of the same commercial soybean oil fatty acid as used in Method A were added 1.5 g of aluminum powder and 0.6 g of aluminum hydroxide, and the resulting mixture was directly distilled to obtain a purified soybean oil fatty acid.

(Method C) To 300 g of the same commercial soybean oil fatty acid as used in Method A were added 1.5 g of aluminum powder and 0.9 g of a copper-zinc alloy catalyst, and the resulting mixture was stirred at 160° C. for 4 hours. Then, the mixture was directly distilled to obtain a purified soybean oil fatty acid.

(Method D) To 300 g of the same commercial soybean oil fatty acid as used in Method A were added 1.5 g of aluminum powder, 0.6 g of aluminum hydroxide and 0.9 g of a copper-zinc alloy catalyst, and the resulting mixture was stirred at 160° C. for 4 hours. Then, the mixture was directly distilled to obtain a purified soybean oil fatty acid.

(Comparative method) 300 g of the same commercial soybean oil fatty acid as used in Method A was distilled without the addition of the reagent to obtain a distilled soybean oil fatty acid.

The result of the test of the above purified soybean oil fatty acids is shown in the following Table 6.

TABLE 6

| Item | Comparative method | Method A | Method B | Method C | Method D |
|---|---|---|---|---|---|
| (1) Distillation yield (wt. %) | 98.3 | 97.0 | 95.9 | 96.1 | 94.7 |
| (2) Color (APHA) | 180 | 60 | 40 | 30 | 20 |
| (3) Heat color stability (APHA) | 300 | 120 | 90 | 70 | 60 |
| (4) Thermal oxidation color stability (Gardner) | 5 | 2–3 | 2 | 1–2 | 1 |
| (5) Base color stability (Gardner) | 7 | 2 | 1–2 | 1 | 1 |
| (6) Acid color stability (Gardner) | 11 | 8 | 6 | 5 | 4 |

EXAMPLE 7

(Method A) To 300 g of a crude coconut oil fatty acid produced from soapstock was added 2.0 g of copper powder, and the resulting mixture was directly distilled to obtain a purified soapstock source coconut oil fatty acid.

(Method B) To 300 g of the same crude coconut oil fatty acid as used in Method A were added 2.0 g of copper powder, 0.3 g of nickel (II) hydroxide and 0.3 g of zinc hydroxide, and the resulting mixture was directly distilled to obtain a purified soapstock source coconut oil fatty acid.

(Method C) To 300 g of the same crude coconut oil fatty acid as used in Method A were added 2.0 g of copper powder and 0.6 g of a raney nickel catalyst, and the resulting mixture was stirred at 140° C. for 4 hours. Then, the mixture was directly distilled to obtain a purified soapstock source coconut oil fatty acid.

(Method D) To 300 g of the same crude coconut oil fatty acid as used in Method A were added 2.0 g of copper powder, 0.3 g of nickel (II) hydroxide, 0.3 g of zinc hydroxide and 0.6 g of a Raney nickel catalyst, and the resulting mixture was stirred at 140° C. for 4 hours. Then, the mixture was directly distilled to obtain a purified soapstock source coconut oil fatty acid.

(Comparative method) 300 g of the same crude coconut oil fatty acid as used in Method A was distilled without the addition of the reagent to obtain a distilled soapstock source coconut oil fatty acid.

The result of the test of the above purified soapstock source coconut oil fatty acids is shown in the following Table 7.

TABLE 7

| Item | Comparative method | Method A | Method B | Method C | Method D |
|---|---|---|---|---|---|
| (1) Distillation yield (wt. %) | 91.3 | 89.1 | 87.2 | 88.1 | 86.0 |
| (2) Color (APHA) | 400 | 100 | 70 | 50 | 40 |
| (3) Heat color stability (APHA) | >500 (Gardner: 5) | 300 | 200 | 180 | 150 |
| (4) Thermal oxidation color stability (Gardner) | 9 | 5 | 4 | 3 | 3 |
| (5) Base color stability (Gardner) | 12 | 5 | 4 | 3 | 2-3 |
| (6) Acid color stability (Gardner) | 7 | 5 | 4 | 3-4 | 3 |

EXAMPLE 8

(Method A) To 300 g of a crude palm oil fatty acid produced from soapstock was added 2.0 g of nickel powder, and the resulting mixture was directly distilled to obtain a purified soapstock source palm oil fatty acid.

(Method B) To 300 g of the same crude palm oil fatty acid as used to Method A were added 2.0 g of nickel powder and 1.0 g of iron (III) hydroxide, and the resulting mixture was directly distilled to obtain a purified soapstock source palm oil fatty acid.

(Method C) To 300 g of the same crude palm oil fatty acid as used in Method A were added 2.0 g of nickel powder and 0.9 g of a molybdenum sulfide catalyst, and the resulting mixture was stirred at 160° C. for 4 hours. Then, the mixture was directly distilled to obtain a purified soapstock source palm oil fatty acid.

(Method D) To 300 g of the same crude palm oil fatty acid as used in Method A were added 2.0 g of nickel powder, 1.0 g of iron (III) hydroxide and 0.9 g of a molybdenum sulfide catalyst, and the resulting mixture was stirred at 160° C. for 4 hours. Then, the mixture was directly distilled to obtain a purified soapstock source palm oil fatty acid.

(Comparative method) 300 g of the same crude palm oil fatty acid as used in Method A was distilled without the addition of the reagent to obtain a distilled soapstock source palm oil fatty acid.

The result of the test of the above purified soapstock source palm oil fatty acids is shown in the following Table 8.

TABLE 8

| Item | Comparative method | Method A | Method B | Method C | Method D |
|---|---|---|---|---|---|
| (1) Distillation yield (wt. %) | 93.1 | 92.2 | 90.5 | 91.3 | 89.4 |
| (2) Color (APHA) | 250 | 150 | 120 | 90 | 70 |
| (3) Heat color stability (APHA) | 400 | 250 | 190 | 150 | 120 |
| (4) Thermal oxidation color stability (Gardner) | 4 | 2 | 1-2 | 1 | 1 |
| (5) Base color stability (Gardner) | 5 | 3 | 2 | 1-2 | 1 |
| (6) Acid color stability (Gardner) | 8 | 5 | 4 | 3-4 | 3 |

EXAMPLE 9

(Method A) To 300 g of a commercial paraffin oxidation fatty acid (a mixture of fatty acids having 7-9 carbon atoms) was added 1.0 g of tin powder and 1.0 g of cobalt powder, and the resulting mixture was directly distilled to obtain a purified synthetic fatty acid.

(Method B) To 300 g of the same commercial paraffin oxidation fatty acid as used in Method A were added 1.0 g of tin powder, 1.0 g of cobalt powder and 0.7 g of cobalt hydroxide, and the resulting mixture was directly distilled to obtain a purified synthetic fatty acid.

(Method C) To 300 g of the same commercial paraffin oxidation fatty acid as used in Method A were added 1.0 g of tin powder, 1.0 g of cobalt powder and 0.3 g of a palladium-on-carbon catalyst, and the resulting mixture was stirred at 100° C. for 4 hours. Then, the mixture was filtered and the filtrate was distilled to obtain a purified synthetic fatty acid.

(Method D) To 300 g of the same commercial paraffin oxidation fatty acid as used in Method A were added 1.0 g of tin powder, 1.0 g cobalt powder, 0.7 g of cobalt hydroxide and 0.3 g of a palladium-on-carbon catalyst, and the resulting mixture was stirred at 100° C. for 4 hours. Then the mixture was filtered and the filtrate was distilled to obtain a purified synthetic fatty acid.

(Comparative method) 300 g of the same commercial paraffin oxidation fatty acid as used in Method A was distilled without the addition of the reagent to obtain a distilled synthetic fatty acid.

The result of the test of the above purified synthetic fatty acids is shown in the following Table 9.

TABLE 9

| Item | Comparative method | Method A | Method B | Method C | Method D |
|---|---|---|---|---|---|
| (1) Distillation yield (wt. %) | 98.9 | 97.3 | 96.5 | 97.2 | 96.6 |
| (2) Color (APHA) | 100 | 40 | 30 | 20 | 15 |
| (3) Heat color stability (APHA) | 300 | 150 | 100 | 60 | 50 |
| (4) Thermal oxidation color stability (Gardner) | 5 | 3 | 2 | 1-2 | 1 |
| (5) Base color stability (Gardner) | 11 | 7 | 6 | 5 | 4-5 |
| (6) Acid color stability (Gardner) | 8 | 5 | 4 | 3-4 | 3 |

EXAMPLE 10

(Method A) To 300 g of a commerical isostearic acid produced from tall oil fatty acid was added 1.5 g of calcium-zinc alloy powder, and the resulting mixture was stirred at 160° C. for 4 hours. Then, the mixture was filtered, and the filtrate was distilled to obtain a purified isostearic acid.

(Method B) To 300 g of the same commerical isostearic acid as used in Method A were added 1.5 g of calcium-zinc alloy powder and 0.5 g magnesium hydroxide, and the resulting mixture was stirred at 160° C. for 4 hours. Then the mixture was filtered, and the filtrate was distilled to obtain a purified isostearic acid.

(Method C) To 300 g of the same commerical isostearic acid as used in Method A were added 1.5 g of calcium-zinc alloy powder and 0.3 g of a rhodium-platinum catalyst, and the resulting mixture was stirred at 160° C. for 4 hours. Then, the mixture was filtered, and the filtrate was distilled to obtain a purified isostearic acid.

(Method D) To 300 g of the same commerical isostearic acid as used in Method A were added 1.5 g of calcium-zinc alloy powder, 0.5 g of calcium hydroxide and 0.3 g of a rhodium-platinum catalyst, and the resulting mixture was stirred at 160° C. for 4 hours. Then, the mixture was filtered, and the filtrate was distilled to obtain a purified isostearic acid.

(Comparative method) 300 g of the same commerical isostearic acid as used in Method A was distilled without the addition of the reagent to obtain a distilled isostearic acid.

The result of the test of the above purified isostearic acids is shown in the following Table 10.

TABLE 10

| Item | Comparative method | Method A | Method B | Method C | Method D |
|---|---|---|---|---|---|
| (1) Distillation yield (wt. %) | 98.7 | 97.3 | 96.4 | 97.3 | 96.4 |
| (2) Color (APHA) | 350 | 130 | 90 | 60 | 40 |
| (3) Heat color stability (APHA) | >500 (Gardner: 5) | 250 | 180 | 130 | 100 |
| (4) Thermal oxidation color stability (Gardner) | 5 | 2-3 | 2 | 1-2 | 1 |
| (5) Base color stability (Gardner) | 7 | 3-4 | 3 | 2-3 | 2 |
| (6) Acid color stability (Gardner) | 9 | 4 | 3-4 | 3 | 2-3 |

It can be seen from the above obtained results that the purified fatty acids obtained in the present invention are remarkably excellent in the color and color stability.

What is claimed is:

1. A method for purifying fatty acids, comprising contacting a fatty acid with both a reducing metal selected from tin, iron, zinc, aluminum, magnesium, copper, calcium, nickel, cobalt and an alloy of these metals in an amount of 0.01-5% by weight based on the amount of a fatty acid to be purified, and a hydrogenation catalyst selected from palladium black, palladium on carbon, platinum oxide, nickel or kieselguhr, Raney nickel, Raney iron, Raney copper, copper-chromite, molybdenum sulfide, platinum on carbon, nickel-hardened fat and rhodium-platinum in an amount of 0.01-5% by weight based on the amount of a fatty acid to be purified, and distilling the treated fatty acid.

2. A method according to claim 1, wherein the treated fatty acid is directly distilled without filtration.

3. A method according to claim 1, wherein the treated fatty acid is filtered, and the filtrate is distilled.

4. A method according to claim 1, wherein the reducing metal and the hydrogenation catalyst are used in combination with a hydroxide of reducing metal selected from tin hydroxide, iron hydroxide, zinc hydroxide, aluminum hydroxide, magnesium hydroxide, copper hydroxide, calcium hydroxide, nickel hydroxide, and cobalt hydroxide in an amount of 0.1-5% weight based on the amount of a fatty acid to be purified.

* * * * *

UNITED STATES PATENT AND TRADEMARK OFFICE
CERTIFICATE OF CORRECTION

PATENT NO. : 4,957,662

DATED : September 18, 1990

INVENTOR(S) : Masao SUZUKI

It is certified that error appears in the above-identified patent and that said Letters Patent is hereby corrected as shown below:

On the title page please insert the following:

-- [73] Assignee: Nippon Oil and Fats Company, Limited
Tokyo, Japan --

Signed and Sealed this

Third Day of March, 1992

*Attest:*

HARRY F. MANBECK, JR.

*Attesting Officer*

*Commissioner of Patents and Trademarks*